(12) United States Patent
Klotz (10) Patent No.: US 7,400,756 B2
(45) Date of Patent: Jul. 15, 2008

(54) METHOD FOR AUTOMATIC CALIBRATION OF PERFUSION PARAMETER IMAGES

(75) Inventor: Ernst Klotz, Uttenreuth (DE)

(73) Assignee: Siemens Aktiengesellschaft, Munich (DE)

( * ) Notice: Subject to any disclaimer, the term of this patent is extended or adjusted under 35 U.S.C. 154(b) by 892 days.

(21) Appl. No.: 10/910,628

(22) Filed: Aug. 4, 2004

(65) Prior Publication Data

US 2005/0058331 A1  Mar. 17, 2005

(30) Foreign Application Priority Data

Aug. 4, 2003  (DE) .................... 103 35 663

(51) Int. Cl.
*G06K 9/00* (2006.01)

(52) U.S. Cl. ...................... 382/131

(58) Field of Classification Search ......... 382/128–132, 382/254; 128/922; 378/4, 6, 8, 98; 600/420, 600/425, 407, 443
See application file for complete search history.

(56) References Cited

U.S. PATENT DOCUMENTS

| 6,373,920 B1 * | 4/2002 | Hsieh .................... 378/98.11 |
| 6,888,914 B2 * | 5/2005 | Edic .............................. 378/4 |
| 6,891,918 B2 * | 5/2005 | Drummond et al. ............ 378/5 |
| 2002/0161292 A1 * | 10/2002 | Wintermark et al. ........ 600/407 |
| 2002/0177957 A1 * | 11/2002 | Lee ............................. 702/19 |
| 2004/0064038 A1 * | 4/2004 | Bruder et al. ............... 600/425 |
| 2004/0138549 A1 * | 7/2004 | Wintermark et al. ........ 600/407 |
| 2005/0283070 A1 * | 12/2005 | Imielinska et al. .......... 600/425 |

FOREIGN PATENT DOCUMENTS

EP  1 210 910 A1 *  6/2002

OTHER PUBLICATIONS

Matthias König: "Brain perfusion CT in acute stroke: current status", in: European Journal of Radiology, vol. 2003, S. S11-S22.*

Matthias Koenig, et al., "Quantitative Assessment of the Ischemic Brain by Means of Perfusion-Related Parameters Derived From Perfusion CT", Stroke, Feb. 2001, pigs 431-437☐☐.*

(Continued)

*Primary Examiner*—Andrew W. Johns
*Assistant Examiner*—Andrae Allison
(74) *Attorney, Agent, or Firm*—Harness, Dickey & Pierce, P.L.C.

(57) ABSTRACT

A method is for calibration of perfusion parameter images. The image data from tomographic imaging measurements are analyzed using a perfusion model, and perfusion parameter values obtained from the analysis are calibrated with a calibration factor to a physiological normal value. To perform the calibration, an image area which contains several different tissue compositions, and in which approximately normal perfusion conditions can be assumed, is selected from the obtained perfusion parameter image. A frequency analysis of the perfusion parameter values contained in this image area is then performed, and at least one frequency interval is selected which corresponds at least approximately to a frequency interval of the occurrence of perfusion parameter values of a known tissue composition. A mean value is calculated from the perfusion parameter values in the frequency interval, and a comparison with the physiological normal value for this tissue composition is made in order to determine the calibration factor or a calibration value included in the calibration factor. The method permits automatic or substantially automatic calibration of perfusion parameter images.

24 Claims, 6 Drawing Sheets

OTHER PUBLICATIONS

Ernst Klotz, et al., "Perfusion measurements of the brain: using dynamic CT for the quantitative assessment of cerebral ischemia in acute stroke", European Journal of Radioloigy 30 (1999), pBs. 170-184☐☐.*

A. Gregory Sorensen, "What is the meaning of Quantitative CBF?", AJNR, Feb. 22, 2001, pp. 235-236.*

Duane D. Blatter, et al., "Quantitative Volumetiric Analysis of Brain MR: Normative Database Spanning 5 Decades of Life", Am J Neuroradiol, Feb. 1995, pigs. 241-251.*

M. König, et al., "CT- perfusion imaging in acute ischemic stroke: comparison of perfusion maps and conventional CT findings", Georg Thieme Verlag Stuttgart, New York, ISSN 1438-9029, pp. 219-226.

Matthias Koenig, et al., "Quantitative Assessment of the Ischemic Brain by Means of Perfusion-Related Parameters Derived From Perfusion CT", Stroke, Feb. 2001, pp. 431-437.

M. König, et al., "Cerebral perfusion CT-theoretical aspects, practical implementation and clinical experience in acute ischemic stroke", Fortschr Röntgenstr 2000; 172: 210-218.

Ernst Klotz, et al., "Perfusion measurements of the brain: using dynamic CT for the quantitative assessment of cerebral ischemia in acute stroke", Rruropean Journal of Radiology 30 (1999), pp. 170-184.

A. Gregory Sorensen, "What is the meaning of Quantitative CBF?", AJNR, Feb. 22, 2001, pp. 235-236.

Duane D. Blatter, et al., "Quantitative Volumetiric Analysis of Brain MR: Normative Database Spanning 5 Decades of Life", Am J Neuroradiol, Feb. 1995, pp. 241-151.

Matthias König: "Brain perfusion CT in acute stroke: current status", in: European Journal of Radiology, vol. 45, 2003, S. S11-S22.

* cited by examiner

METHOD FOR AUTOMATIC CALIBRATION OF PERFUSION PARAMETER IMAGES

The present application hereby claims priority under 35 U.S.C. § 119 on German patent application number DE 103 35 663.0 filed Aug. 4, 2003, the entire contents of which are hereby incorporated herein by reference.

FIELD OF THE INVENTION

The present invention generally relates to a method for calibration of perfusion parameter images, in particular of the brain. Preferably, in the method, the image data from several images of an examination volume which have been generated in chronological succession using a tomographic imaging method are made ready. The image data are then preferably analyzed using a perfusion model in order to obtain perfusion parameter values of the examination volume with spatial resolution, and the perfusion parameter values obtained from the analysis are preferably calibrated with a calibration factor to a physiological normal value. The calibrated perfusion parameter values obtained in this way can then be presented in a calibrated perfusion parameter image.

BACKGROUND OF THE INVENTION

Image-producing perfusion measurements of organs represent an important tool in medical diagnosis. This applies particularly to the measurement of cerebral perfusion parameters which are used to present acute cerebral perfusion disorders, for example in the diagnosis of ischemic cerebral infarct. When measuring perfusion parameters, for example cerebral blood flow (CBF) or cerebral blood volume (CBV), several tomographic images of the same examination volume, generally sectional images of a predetermined layer of the brain, are taken in chronological succession following injection of a contrast medium bolus and are analyzed to determine the perfusion parameters.

Most imaging methods for determining brain perfusion parameters use tracer-kinetic models with which the perfusion parameters from the image data of the image are calculated in order then to present the perfusion parameters in image form. These perfusion parameter images then make it possible, for example, to assess the degree of severity and extent of ischemia.

Examples of models used, and the determination of various perfusion parameters in cerebral perfusion computed tomography, are set out in the publications by M. König et al., "CT-Perfusionsbildgebung beim akuten ischämischen Hirninfarkt: Vergleich von Parameter-bildern der zerebralen Perfusion und Nativ-CT-Befunden", [CT perfusion imaging in acute ischemic cerebral infarct: Comparison of parameter images of cerebral perfusion and native CT findings], Fortschr Röntgenstr 2000, 172, pages 219-226, and M. König et al., "Zerebrale Perfusions-CT: Theoretische Grundlagen, methodische Realisierung und praktische Erfahrungen in der Diagnostik des ischämischen Hirninfarktes" [Cerebral perfusion CT: Theoretical principles, methodology and practical experience in diagnosis of ischemic cerebral infarct], Fortschr Röntengstr 2000, 172, pages 210-218. The perfusion computed tomography used here has the advantage, compared to other imaging methods, that changes in concentration of the contrast medium in the vessel system are reflected directly in a proportional change of the CT values.

Nowadays, in addition to simple sectional images of the brain, it is possible, using multisection computed tomography, to measure larger volume areas of the brain or of other organs by simultaneous recording of several parallel sections.

The need to use models to determine the perfusion parameters from the image data often leads to methodology problems, since either it is not possible to produce an optimal injection bolus, or one of the parameters needed for the determination cannot be recorded with sufficient absolute accuracy. Although the perfusion parameter images obtained do then correctly reflect the relative perfusion conditions within the measured examination volume, they are associated with a patient-dependent, systematic error, which makes determination of the absolute values difficult. This is not an actual limitation for clinical diagnosis, because the image impression in most cases already permits adequate diagnosis, and relative values permit a quantitative analysis (cf. M. König et al.; "Quantitative Assessment of the Ischemic Brain by Means of Perfusion-Related Parameters Derived from Perfusion CT"; Stroke 2001; 32: 431-437).-However, a calibration to physiological normal values is desirable because, among other things, it permits normalized color image presentation, which greatly increases acceptance by users, for example neurologists.

In a known technique for calibration of perfusion parameter images, an ROI (region of interest) is placed manually in an anatomically coherent region of known tissue composition, and the perfusion parameter value in this ROI is determined. From the relationship of this value and an assumed physiological normal value for this tissue composition it is possible to determine, for the entire image, a calibration factor with which all perfusion parameter values of the image are scaled.

However, this procedure has some disadvantages. Thus, the ROI has to be positioned manually and its size must be adapted in order to obtain an image area of homogeneous composition. Because of the substantial layer thicknesses which are needed for adequate contrast in image-producing perfusion measurements, there are only a few areas of really homogeneous tissue composition. This applies above all to the gray matter of the brain, in respect of which corresponding ROIs must be chosen very small. Although larger cerebral medulla areas can be selected, these have lower perfusion parameter values, with the result that they produce more noise. In elderly patients, the values in these areas are also much more variable.

SUMMARY OF THE INVENTION

An object of an embodiment of the present invention is to make available a method for calibration of perfusion parameter images which permits substantial automation of the calibration.

This object may be achieved with a method. Advantageous developments of the method can be taken from the following description and the illustrative embodiments.

In an embodiment of the present method for calibration of perfusion parameter images, the image data from several images of an examination volume which have been generated in chronological succession using a tomographic imaging method are made ready, the image data are analyzed using a perfusion model in order to obtain perfusion parameter values of the examination volume with spatial resolution, and the perfusion parameter values obtained from the analysis are calibrated with a calibration factor to a physiological normal value. An embodiment of the present method includes the following steps for performing the calibration.

First, an image area which contains several different tissue compositions, and in which approximately normal perfusion conditions can be assumed, is selected from a perfusion parameter image generated from the non-calibrated perfusion parameter values. A frequency analysis of the perfusion parameter values contained in this image area is then performed, and at least one frequency interval is selected which corresponds at least approximately to a frequency interval of the occurrence of perfusion parameter values of a known tissue composition in the selected image area. A mean value is calculated from the perfusion parameter values in the selected frequency interval, and a comparison of this mean value and the physiological normal value for the known tissue composition is made to determine the calibration factor or a calibration value included in the calibration factor.

If only one frequency interval is selected, the calibration factor is determined directly. If several frequency intervals are selected, calibration values are determined which correspond to individual calibration factors for each selected tissue composition and from which the (total) calibration factor is obtained by averaging.

In an embodiment of the present method, it is no longer necessary to manually adapt an ROI to an anatomically coherent region of an individual known tissue composition. The image area to be selected in the present method can instead be chosen much larger, the only consideration being to position it in an area with approximately normal, i.e. non-ischemic, perfusion conditions, for example in the non-ischemic hemisphere in the case of acute stroke.

By way of automatic analysis of the frequency distribution of the perfusion parameter values in the selected image area, the calibration of the perfusion parameter values can take place completely automatically when the frequency interval and the physiological normal value are defined. The method is especially suitable for use in, for example, perfusion CT based on iodine contrast medium, in particular for calibration of the parameters of cerebral blood flow (CBF) and cerebral blood volume (CBV). However, the method is equally suitable for other tomographic imaging methods, for example xenon CT, perfusion imaging with MRI or magnetic resonance tomography, for example by means of gadolinium bolus tracking, or for nuclear medicine measurement techniques such as PET (positron emission tomography) or SPECT (single photon emission computed tomography).

The image area selected for the frequency analysis is preferably so large that it is possible to assume that the frequency distribution of tissue compositions contained therein corresponds at least approximately to the frequency distribution of the tissue compositions in the whole of the examination volume. Since the frequency distribution of the tissue compositions occurring in an examination volume, in particular of a section of the examination object generated by an imaging method, is generally roughly known and different tissue compositions also have different perfusion parameter values, a specific tissue composition can be assigned to individual frequency intervals within the frequency distribution of the perfusion parameter values. The histogram obtained from the image area by way of the frequency analysis is in this case preferably divided into several interval ranges which are each assigned to individual tissue compositions. From these intervals, it is then possible to select the suitable frequency interval for the averaging. These intervals are formed, and the suitable interval selected, preferably on the basis of a cumulative histogram.

In a particularly advantageous embodiment, the image area is selected such that it corresponds at least approximately to half of the examination volume, for example to a half of the recorded brain section. In doing this, the axis of symmetry of the examined object is taken into consideration, the half selected for the image area corresponding to the symmetry half in which perfusion is not disturbed. The selection of the non-ischemic half can in this case take place automatically by comparison of the perfusion parameter values obtained in both halves, and the half with the higher values is then used, for example, for assessing the blood flow.

In a development of an embodiment of the present method, it is also possible to select several frequency intervals in order to calculate, for each selected frequency interval, a mean value of the perfusion parameter values and to determine a calibration value with the corresponding physiological normal value. The calibration factor used for calibration of the perfusion parameter values can then be obtained by averaging the individual calibration values.

In one embodiment of the present method, the frequency distribution of different tissue compositions in the selected image area can also be determined to start with from the images of the examination volume.

BRIEF DESCRIPTION OF THE DRAWINGS

The present method is explained in more detail below on the basis of an illustrative embodiment and in conjunction with the figures, in which.

DETAILED DESCRIPTION OF THE PREFERRED EMBODIMENTS

Figure 1:
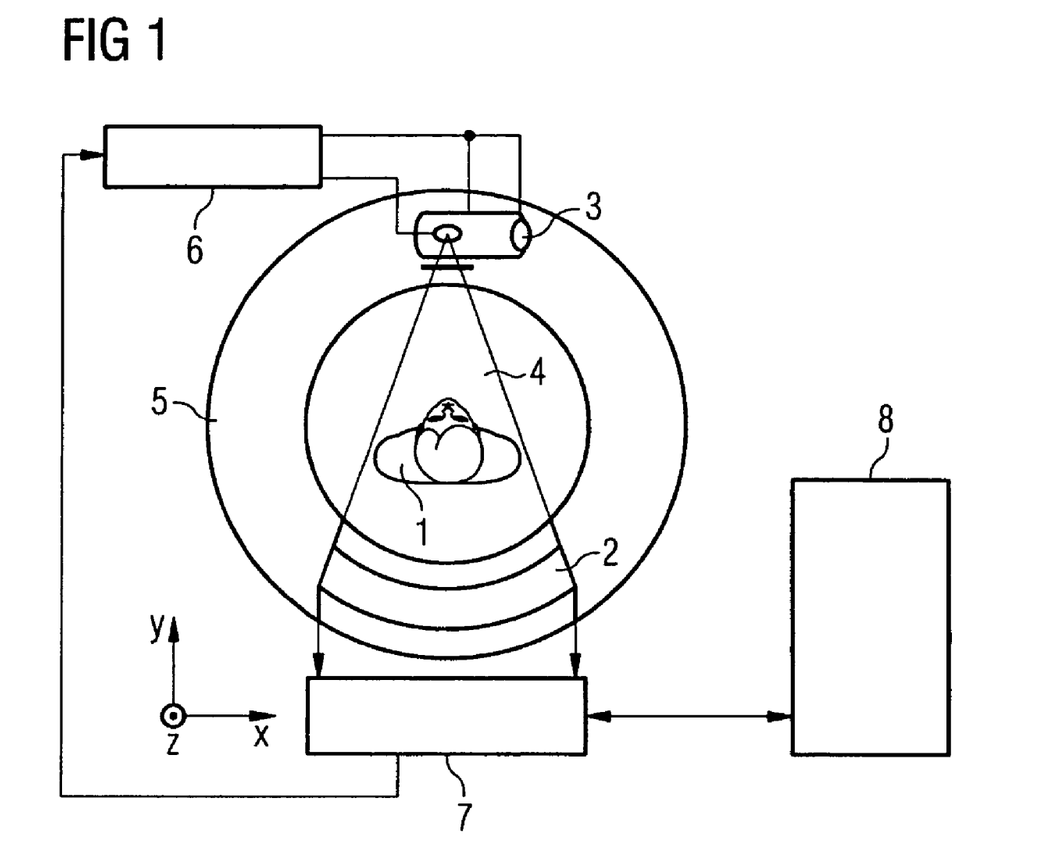
FIG. 1 shows a diagrammatic representation of an example of a computed tomography installation for performing perfusion computed tomography.

FIG. 1 shows a diagrammatic view of an example of a computed tomography installation used for perfusion computed tomography. Using such an installation, it is possible to generate images of a section of a patient's brain in chronological succession, from which images a perfusion parameter image can be derived.

Typical section thicknesses in this case are about 10 mm. It is possible, for example, to record an image sequence of 32-40 images at a rate of 1 image per second immediately after injection of a contrast medium bolus.

In a first step, all pixels in the dynamic image series which do not represent brain tissue or vessels are preferably eliminated by way of segmenting. A series of special smoothing operations is then performed in order to minimize the image noise to be expected in pixel-based analysis. From the density/time curves for each pixel, it is then possible to calculate a series of functional images of the cerebral perfusion from which the parameter images of the CBF and of the CBV have attained the greatest prognostic significance.

FIG. 1 depicts an X-ray source in the form of an X-ray tube 3 which emits a fan-shaped X-ray beam bundle 4 in the direction of a detector row with X-ray detector elements 2. Both the X-ray tube 3 and the detector elements 2 are arranged on a gantry 5 which can rotate continuously about a patient 1.

The patient 1 lies on a patient support table (not shown in FIG. 1) extending into the gantry 5. The gantry 5 rotates in an x-y plane of a Cartesian system of coordinates x-y-z shown in FIG. 1. The patient support table for the patient is movable along the z axis, which corresponds to the section thickness direction of the sections of the patient 1 which are to be presented.

The X-ray tube 3 is supplied with high voltage, for example 120 kV, from a high-voltage generator 6. A control device 7 is used to control the individual components of the high-voltage generator 6, the gantry 5, the detector elements 2, and the patient support table (not shown), in order to record measurement data. The measurement data are forwarded to an image computer 8 for image reconstruction and for calculation of the perfusion parameter values from the measurement data.

In the present method, calibration of the perfusion parameter values based on an analysis of the frequency distribution of the parameter values is performed in an image area in which approximately normal, non-ischemic perfusion conditions can be assumed to exist.

This procedure is based on the fact that, in a tomogram of a patient, the frequency of different tissue compositions is reflected in a frequency distribution of the perfusion parameter values. In a typical section through the brain, there are voxels of 4 different compartments:

cerebrospinal fluid (CSF): CBF=0, or only noise, since no perfusion;
white matter (cerebral medulla): CBF ca. 15-30 ml/min/100 g;
gray matter (cortex, stem ganglia): CBF ca. 60-80 ml/min/100 g;
vessels: much higher values (in perfusion CT).

Arrangement of the perfusion parameter values according to their size is therefore in principle possible in the stated sequence of the compartments. Normalizing calibration can be done with respect to the white matter compartment, the gray matter compartment, or, if appropriate, to the whole brain tissue, a combination of the gray matter and white matter compartments. Since the CBF (cerebral blood flow) and the CBV (cerebral blood volume) of the gray matter and white matter in normally perfused areas differ by a factor of 2 to 3, they would in principle be separated on the basis of their values.

The last compartment of the vessels is problematic in the case of intravascular tracers, for example iodine or gadolinium, because it concerns only parenchymal perfusion. The first and last compartments can of course be removed by segmenting, if appropriate even before imaging, but this is often incomplete.

Figure 2:
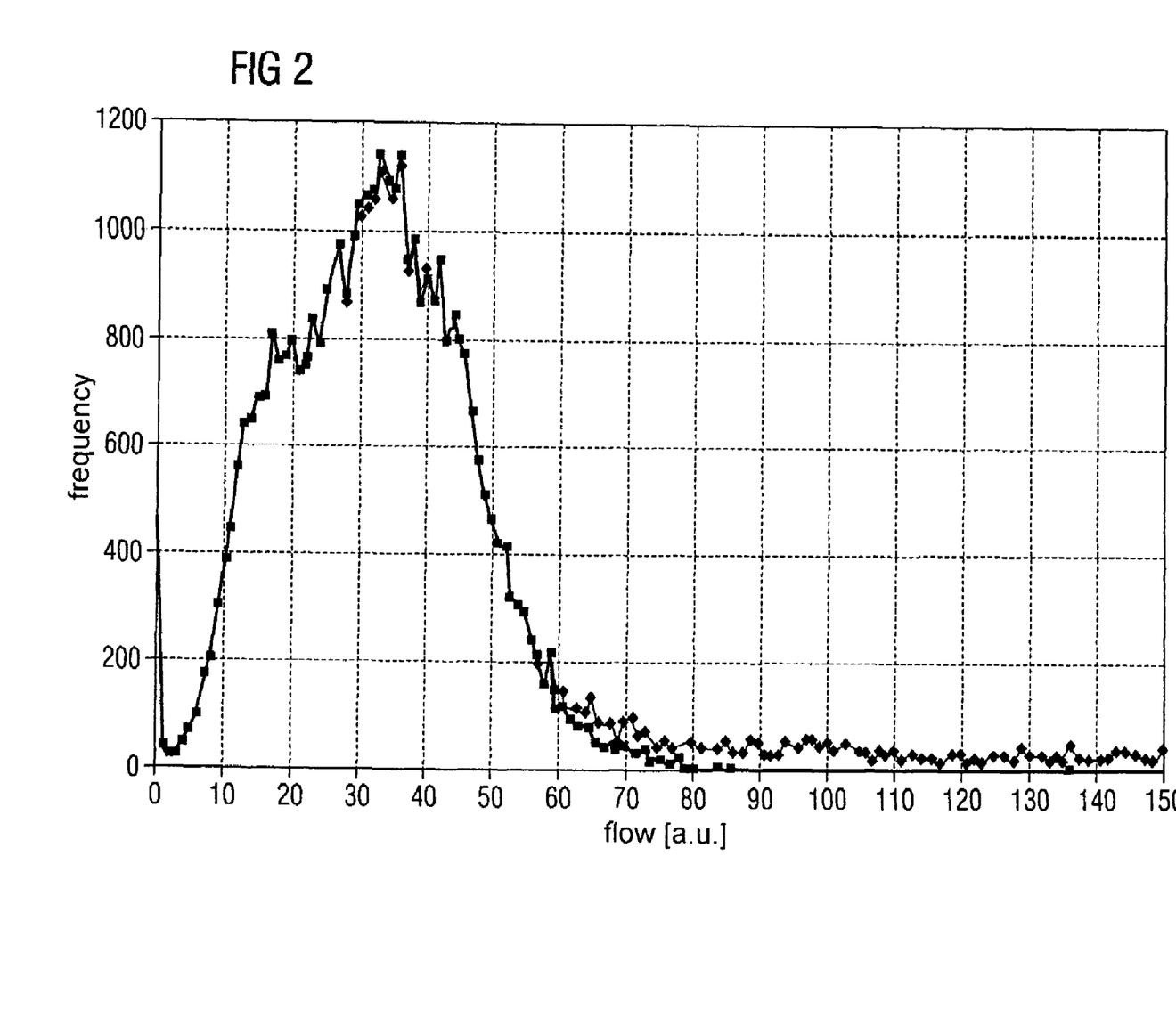
FIG. 2 shows an example of a histogram of a non-ischemic image area.

Moreover, because of the low spatial resolution of the imaging measurement at which section thicknesses of ca. 10 mm are present and in which a resolution is achieved which is in no case better than 2-3 mm, there are only a few voxels which actually belong entirely to only one compartment. Partial volume effects often cause mixing. Because of the additionally high noise, exact separation of the perfusion parameter values according to their size is therefore generally not possible. This can also be seen in FIG. 2 which shows a histogram of a non-ischemic image area. It is evident from this histogram that no two maxima for white brain matter and gray brain matter can be resolved. There is therefore considerable overlapping between gray brain matter and white brain matter in this histogram. The long trail on the right-hand side is caused by pixels with vessel components.

Figure 3:
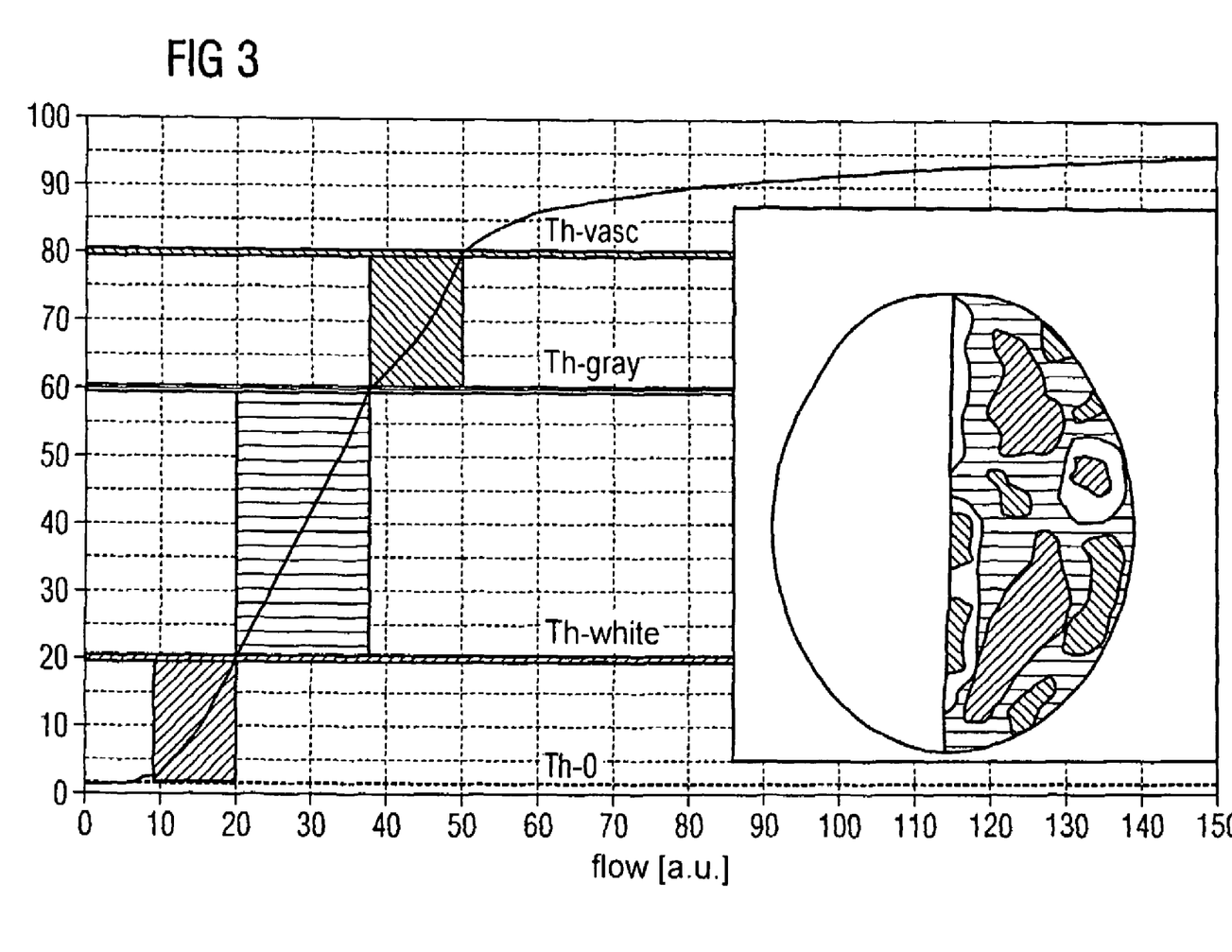
FIG. 3 shows a cumulative histogram of the frequency distribution of FIG. 2, indicating frequency intervals.

In an embodiment of the present method, these problems are remedied by a histogram-based frequency analysis. In a first step thereof, a sufficiently large, non-ischemic image area is identified in the perfusion parameter image obtained. A complete hemisphere of the brain is particularly suitable for this purpose. In the next step, a cumulative histogram of this area is created and, by formation of intervals, is divided into 4 areas:

0<frequency<th-0: CSF, noise pixel
th-0<frequency<th-white: mainly white matter
th-white<frequency<th-gray: gray/white mixed tissue
th-gray<frequency<th-vasc: mainly gray matter
th-vasc<frequency<100%: high vessel content This interval formation is indicated in the cumulative histogram of FIG. 3, which is based on the histogram values of FIG. 2. The mean values of the perfusion parameters are formed in the three middle intervals:

M-low [th-0, th-white]: white matter
M-mid [th-white, th-gray]: mixed matter
M-high [th-gray, th-vasc]: gray matter.

In the present example, these mean values in the three intervals are 14.4, 30.4 and 44.2. One of these three values is then normalized to the corresponding known or assumed physiological normal value of the tissue concerned by this interval. Normalization to a cortical CBF of 75 in this case gives a calibration factor of 75/44.2=1.70, normalization to a total CBF of 50 gives a calibration factor of 50/30.4=1.65. One of these calibration factors is then used for global scaling of the entire image, i.e. of all the perfusion parameter values contained in the image.

Figure 7:
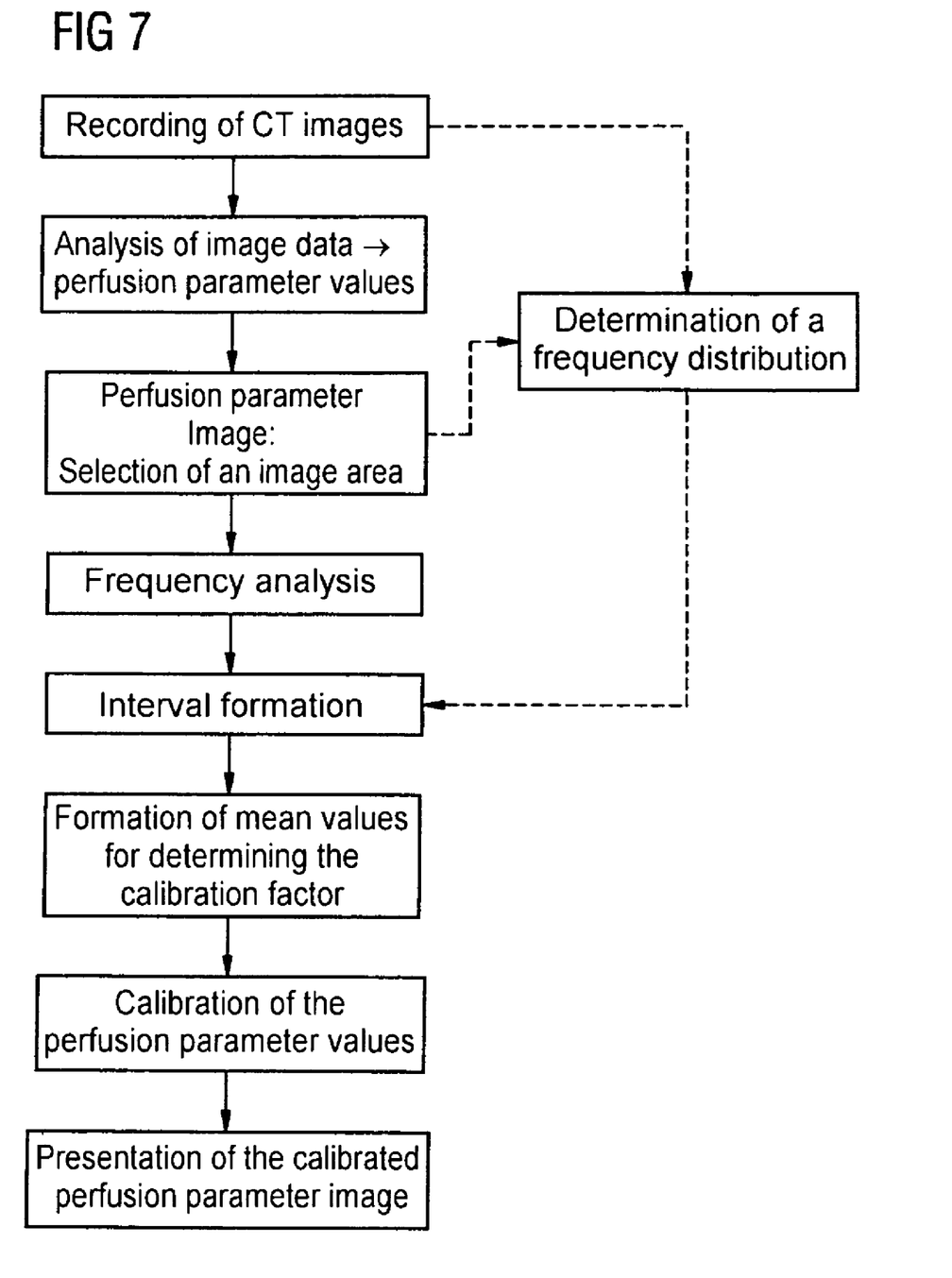
FIG. 7 shows a diagrammatic overview of the method steps.

An overview of the method steps is given in FIG. 7, in which the optional determination of the frequency distribution of tissue compositions in the image area from the CT images is shown by broken lines.

For the division of the cumulative histogram into individual frequency intervals, th-0 can often be assumed as 0. th-vasc has to be determined empirically, because it is dependent on the spatial resolution. Since gray matter and white matter occur with approximately the same frequency in the brain, th-white and th-gray may be arranged symmetrically within th-0 and th-vasc.

Figure 4:
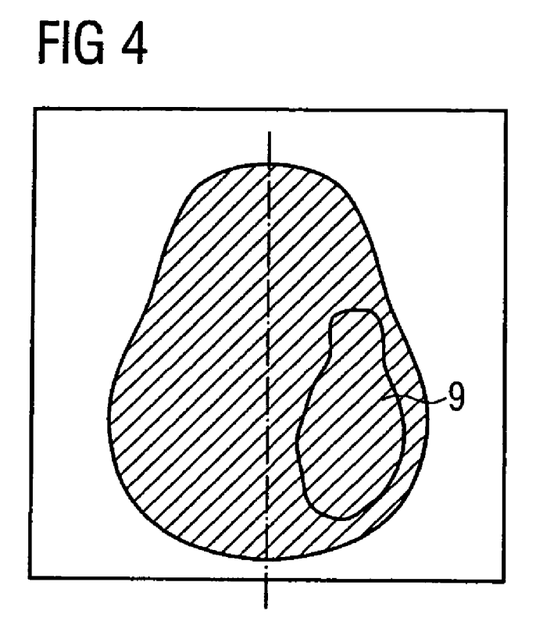
FIG. 4 shows an example of a CBF image (typical color depiction not shown) in which an extensive infarct area is indicated.

An example is given below in which perfusion CT was performed on a patient with acute stroke. FIG. 4 shows a CBF image which is obtained from this measurement, but in which the typical color depiction in the present patent application is not evident. In this color depiction, which is familiar to the skilled person, the perfusion conditions are presented by different colors. For purposes of illustration, an extensive infarct area 9 is identified in the right-hand half of the image.

Figure 5:
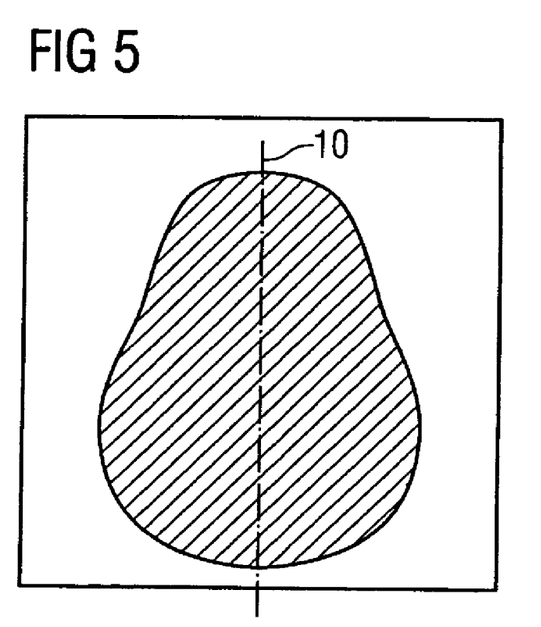
FIG. 5 shows the CBF image from FIG. 4, indicating an automatically determined axis of symmetry for division into the ischemic half and the non-ischemic half.

In the present illustrative embodiment, the axis of symmetry 10 is now determined automatically from the outer contour of the brain in the image, in order to divide the brain in the perfusion parameter image into an ischemic hemisphere and a non-ischemic hemisphere (FIG. 5). The non-ischemic hemisphere is selected as the image area with which the frequency analysis is performed. This can be done completely automatically.

Figure 6:
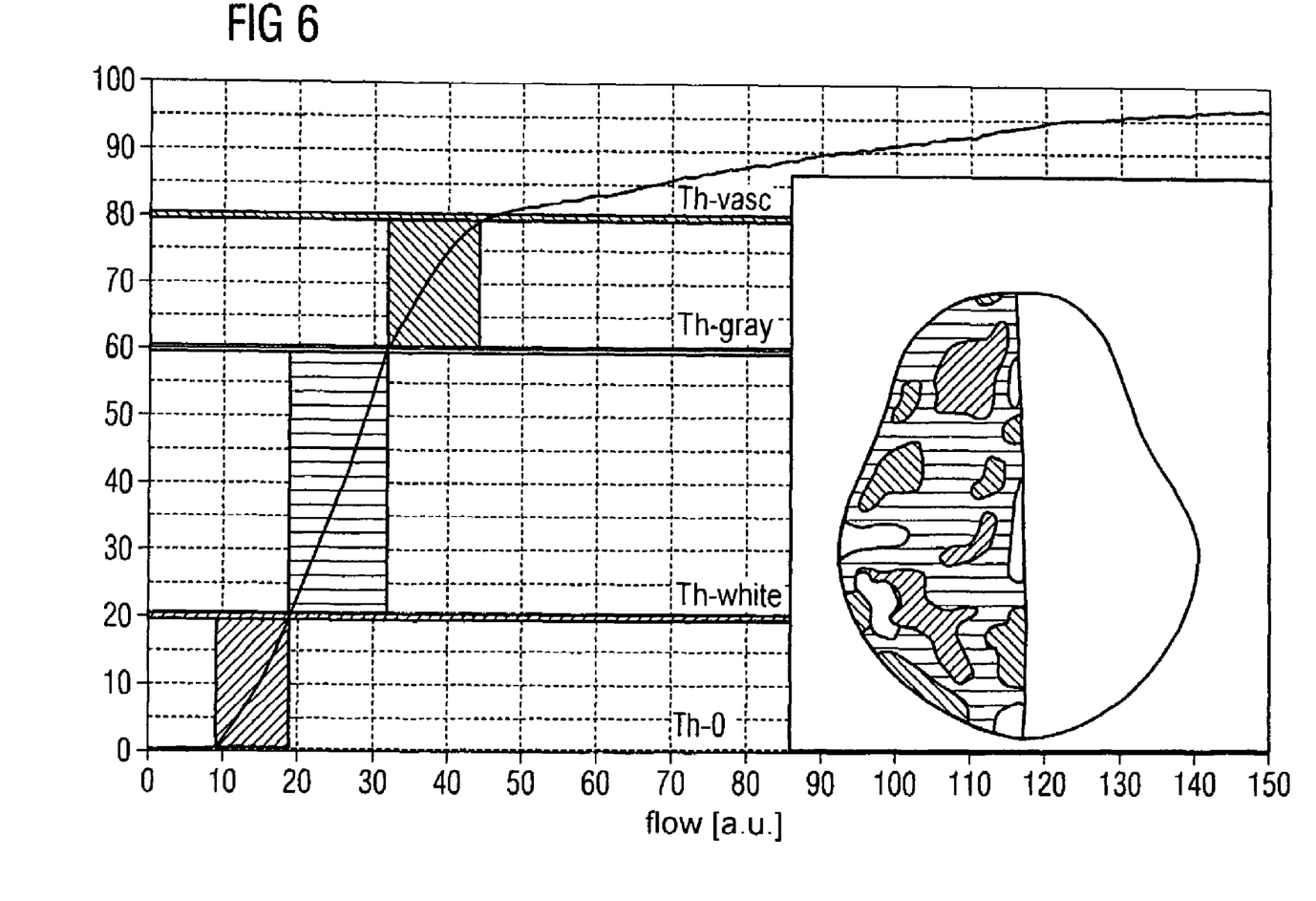
FIG. 6 shows a cumulative histogram of the selected non-ischemic hemisphere from FIG. 5, with the frequency intervals selected therein.

FIG. 6 shows the cumulative histogram of this non-ischemic hemisphere. The thresholds for the subdivision into the individual frequency intervals were in this case selected with th-0=0, th-white=20%, th-gray=60%, and th-vasc=80%. For normalization, the mean value in the middle interval, which corresponds to a mixed tissue of gray matter and of white matter, is determined at 26.5. By normalization to the total CBF of 50, this gives a calibration factor 50/26.5=1.89.

All the perfusion parameter values of FIG. 4 are multiplied by this calibration factor in order to obtain a calibrated perfusion parameter image. This image appears to be identical to that in FIG. 4, but the CBF values, which are scaled in color in the image, are now at the correct level.

Therefore, the person looking at this image now has more reliable information concerning the absolute level of the corresponding perfusion parameters. As in the present example, the entire method can be completely automated. In cases where the perfusion disturbances are not present in one symmetry half of the examination volume, it is possible either for the user to initially select a rough image area, after which the subsequent calculations take place in an automated manner, or the selection likewise takes place in an automated manner by automatic evaluation of the perfusion parameter values and comparison of the values of different image areas.

Exemplary embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for calibration of perfusion parameter images, wherein image data from several images of an examination volume which have been generated in chronological succession using a tomographic imaging method are made ready, the method comprising:

analyzing the image data using a perfusion model in order to obtain perfusion parameter values of the examination volume with spatial resolution;

calibrating perfusion parameter values, obtained from the analysis, with a calibration factor to a physiological normal value, the calibration including, selecting an image area, which contains several different tissue compositions and in which approximately normal perfusion conditions are assumable, from a perfusion parameter image generated from the perfusion parameter values, performing a frequency analysis of the perfusion parameter values contained in the selected image area, selecting at least one frequency interval, which corresponds at least approximately to a frequency interval of the occurrence of perfusion parameter values of a known tissue composition, calculating a mean value of the perfusion parameter values in the selected at least one frequency interval, and performing a comparison with the physiological normal value for this tissue composition to determine at least one of the calibration factor and a calibration value included in the calibration factor.

2. The method as claimed in claim 1, wherein, in the frequency analysis, a cumulative histogram is created from which the frequency interval is selected.

3. The method as claimed in claim 1, wherein the image area is selected with a size in which a frequency distribution of tissue compositions present in the entire examination volume corresponds at least approximately to the frequency distribution in the selected image area.

4. The method as claimed in claim 1, wherein the image area is selected such that it corresponds at least approximately to half the extent of the examination volume in the image.

5. The method as claimed in claim 1, wherein, before performing the calibration, at least one of the images of the examination volume is used to determine a frequency distribution of the different tissue compositions in the image area, in order to obtain the frequency interval of the occurrence of the known tissue composition in the image area.

6. The method as claimed in claim 1, wherein the method is performed for calibration of perfusion parameter images of the brain.

7. The method as claimed in claim 6, wherein the known tissue composition selected is at least one of white brain matter, gray brain matter, and a mixture of white and gray brain matter.

8. The method as claimed in claim 6, wherein a complete hemisphere of the brain is selected as image area.

9. The method as claimed in claim 1, wherein at least one of blood flow and blood volume are obtained as perfusion parameter values and calibrated.

10. The method as claimed in claim 1, wherein the calibrated perfusion parameter values are presented as a calibrated perfusion parameter image.

11. The method as claimed in claim 1, wherein the images of the examination volume are generated by at least one of perfusion computed tomography and xenon computed tomography.

12. The method as claimed in claim 1, wherein the images of the examination volume are generated by magnetic resonance tomography.

13. The method as claimed in claim 1, wherein the images of the examination volume are generated by a nuclear medicine measurement technique.

14. The method as claimed in claim 1, wherein, when the frequency interval and the physiological normal value are defined, the frequency analysis, the calculation of the mean value, the determination of the calibration factor and the calibration of the perfusion parameter values with this calibration factor are performed automatically after selection of the image area.

15. The method as claimed in claim 1, wherein several frequency intervals are selected in order to obtain several calibration values from which the calibration factor is determined by averaging.

16. The method as claimed in claim 2, wherein the image area is selected with a size in which a frequency distribution of tissue compositions present in the entire examination volume corresponds at least approximately to the frequency distribution in the selected image area.

17. The method as claimed in claim 7, wherein a complete hemisphere of the brain is selected as image area.

18. A method for calibration of perfusion parameter images, wherein image data from tomographic imaging measurements are analyzed using a perfusion model, and perfusion parameter values obtained from the analysis are calibrated with a calibration factor to a physiological normal value, the method comprising:

selecting an image area, which contains several different tissue compositions and in which approximately normal perfusion conditions are assumable, from a perfusion parameter image generated from the perfusion parameter values;

performing a frequency analysis of the perfusion parameter values contained in the selected image area;

selecting at least one frequency interval, which corresponds at least approximately to a frequency interval of the occurrence of perfusion parameter values of a known tissue composition;

calculating a mean value of the perfusion parameter values in the selected at least one frequency interval; and performing a comparison with the physiological normal value for this tissue composition to determine at least one of the calibration factor and a calibration value included in the calibration factor.

19. The method as claimed in claim 18, wherein, in the frequency analysis, a cumulative histogram is created from which the frequency interval is selected.

20. The method as claimed in claim 18, wherein the image area is selected with a size in which a frequency distribution of tissue compositions present in the entire examination volume corresponds at least approximately to the frequency distribution in the selected image area.

21. The method as claimed in claim 18, wherein the image area is selected such that it corresponds at least approximately to half the extent of the examination volume in the image.

22. The method as claimed in claim 1, wherein the method is for calibration of perfusion parameter images of the brain.

23. The method as claimed in claim 18, wherein the method is for calibration of perfusion parameter images of the brain.

24. An apparatus for calibration of perfusion parameter images, wherein image data from tomographic imaging measurements are analyzed using a perfusion model, and perfusion parameter values obtained from the analysis are calibrated with a calibration factor to a physiological normal value, the apparatus comprising:

means for selecting an image area, which contains several different tissue compositions and in which approximately normal perfusion conditions are assumable, from a perfusion parameter image generated from the perfusion parameter values;

means for performing a frequency analysis of the perfusion parameter values contained in the selected image area;

means for selecting at least one frequency interval, which corresponds at least approximately to a frequency interval of the occurrence of perfusion parameter values of a known tissue composition;

means for calculating a mean value of the perfusion parameter values in the selected at least one frequency interval; and means for performing a comparison with the physiological normal value for this tissue composition to determine at least one of the calibration factor and a calibration value included in the calibration factor.

* * * * *